United States Patent [19]
Hassler

[11] 3,974,692
[45] Aug. 17, 1976

[54] APPARATUS FOR THE MEASUREMENT OF THE VELOCITY OF MEDIA FLOWING IN CONDUITS

[75] Inventor: Dieter Hassler, Erlangen, Germany

[73] Assignee: Siemens Aktiengesellschaft, Erlangen, Germany

[22] Filed: Aug. 14, 1974

[21] Appl. No.: 497,496

[30] Foreign Application Priority Data
Aug. 16, 1973  Germany............................ 2341476

[52] U.S. Cl............................. 73/194 A; 128/2.05 F
[51] Int. Cl.²........................................... G01F 1/66
[58] Field of Search ............. 73/194 A; 128/2.05 F, 128/2.05 Z

[56] References Cited
UNITED STATES PATENTS 3,766,517  10/1973  Fahrbach..................... 73/194 A X
3,777,740  12/1973  Hokanson ................. 128/2.05 Z X

OTHER PUBLICATIONS

D. W. Baker "Pulsed Ultrasonic Doppler Blood–Flow Sensing", IEEE Transactions on Sonics and Ultrasonics, vol. SU–17, No. 3, July 1970, pp. 170–184.

*Primary Examiner*—Charles A. Ruehl
*Attorney, Agent, or Firm*—Haseltine, Lake & Waters

[57] ABSTRACT

An apparatus for the measurement of the velocity of media which flow particularly in conduits, for example, blood in its vessels, through the intermediary of ultrasound according to the Doppler effect-method. The apparatus includes at least two ultrasonic transmitter-receivers for the inclined transmission of the ultrasound into the media and for receiving of the ultrasound reflected by the medium, as well as an installation for determining from the frequencies of the emitted and received ultrasound, a value which is proportional to the flow velocity of the medium.

13 Claims, 3 Drawing Figures

3,974,692

APPARATUS FOR THE MEASUREMENT OF THE VELOCITY OF MEDIA FLOWING IN CONDUITS

FIELD OF THE INVENTION

The present invention relates to an apparatus for the measurement of the velocity of media which flow particularly in conduits, for example, blood in its vessels, through the intermediary of ultrasound according to the Doppler effect-method. The apparatus includes at least two ultrasonic transmitter-receivers for the inclined transmission of the ultrasound into the media and for receiving of the ultrasonics reflected by the medium, as well as an installation for determining, from the frequencies of the emitted and received ultrasound, a value which is proportional to the flow velocity of the medium.

In the measurement of the velocity of flowing medium by means of ultrasound according to the Doppler effect-method, a problem is encountered in that the frequency of the received Doppler signals which are employed for measurement of the velocity of flowing media, are dependent, as inherently desired, not upon the flow velocity alone, but also upon the entering beam angle of the ultrasound into the medium.

DISCUSSION OF THE PRIOR ART

An apparatus of the above-described type has become known from German Published Specification No. 1,798,104, in particular for the measurement of blood flow velocity wherein the entering beam angle ($\theta$) is eliminated through the beaming in of ultrasound from two transmitting directions which subtend an angle of 90°, and the subsequent calculation of the two different Doppler frequencies $\Delta f_1$ and $\Delta f_2$ obtained from the mutually perpendicular directions into $\Delta f_1^2 + \Delta f_2^2 = k^2 \cdot (\sin^2\phi + \cos^2\phi)$.

However, the apparatus according to German Published Specification No. 1,798,104 can be successfully utilized only under particular predetermined external measuring preconditions. Thus, for example, in order to obtain satisfactory measured results, it must be feasible that both of the separated transmitting lobes of the 90°-receiver contact one and the same blood vessel, and not possibly two different, superimposed lying blood vessels. A correct locating procedure of that kind requires a considerable degree of skill by the examining person upon the application of the receiver and, particularly, also requires knowledge of the approximate physical position of the artery which is to be located within the body. The absolutely necessary free access of sound to the blood vessel which is to be located from two sides thereof, furthermore limits, to a not insignificant extent, the area of application for the receiver to the overall body. Furthermore, for example, the fixed 90°-position of the transmitter-receivers prevents the application of the receiver to relatively sharply curved body portions, and the relatively restricted linear displaceability of the transmitter-receivers relative to each other (physical measurements by the receiver should be relatively small), practically allows for only the measurement of blood vessels which are relatively proximate to the surface of the body. Furthermore, it must also be considered that the Doppler frequencies $\Delta f_1$ and, respectively, $\Delta f_2$ in the apparatus of German Published Specification No. 1,798,104 do not deal with a single frequency, but with an entire frequency mixture. The inherently applicable relevant frequencies utilized for the equation $\Delta f_1^2 + \Delta f_2^2$ thus merely provide median frequencies, which must first be determined from the entire spectrum of the particular Doppler signal in accordance with a predetermined measuring and/or calculating method. For example, in German Laid-Open Specification 1,791,191, there is described such a method for determining the median frequency. In order to carry out the foregoing, on the one hand, there is required a measuring installation which selects predetermined frequencies from the Doppler signals and measures their intensities (twelve band filters tuned to different Doppler frequencies with subsequently switched-in-peak detectors). On the other hand, there is also required an electronic calculating installation with a plurality of individual calculating elements (multipliers, summators, divider elements), which calculate from the particular measured intensities ($S_1 \ldots _n$), the median frequencies ($f_a \ldots _n$) of the band filters, as well as the frequency spacings $\Delta f$ of a weighted median value $\bar{f}_D$ of the entire Doppler signal-frequency spectrum to $$\bar{f}_D = \frac{\overset{n}{\underset{a}{\epsilon}} (S_{a \ldots n} \cdot f_{a \ldots n}) \Delta f}{\overset{n}{\underset{a}{\epsilon}} S_{a \ldots n} \Delta f}$$

It is easily ascertainable that the determination of a single median Doppler frequency requires relatively highly complex circuitry. In the apparatus according to German Published Specification No. 1,798,104 this technical requirement must be doubled since, in order to eliminate the inlet beam angle, two such Doppler frequencies must be concurrently processed.

SUMMARY OF THE INVENTION

Accordingly, it is an object of the present invention to provide an apparatus for the measurement of the velocity of media which flow particularly in conduits by means of ultrasound pursuant to the Doppler method which, similar to the apparatus disclosed in German Published Specification No. 1,798,104, allows for an angularly-independent measurement, but whose receiver is, however, at the smallest geometric construction simpler and for measuring purposes essentially more assuredly applicable then the receiver of the apparatus according to the German Published Specification. Furthermore, in the inventive apparatus, it is also particularly feasible, that the pre-processing of the Doppler signals, under certain conditions, in the described context, may be effectuated at a considerably reduced practical requirement in contrast with the apparatus pursuant to German Published Specification No. 1,798,104 such as, for example, with only a single measuring and calculating circuit according to German Laid-Open Specification No. 1,791,191, or any similar circuit.

The foregoing object is inventively achieved in that both transmitters-receivers are located at a predetermined spacing adjacent each other, in a manner, whereby their transmitting-receiving directions extend in parallel, and have associated therewith an installation for the measurement of the difference in time between the receipt of the ultrasound reflected by the flowing medium at the first and a second ultrasonic transmitter-receivers after at the two transmitter-receivers preferably concurrently achieved reflection of the ultrasound in the medium, and wherein means are provided for indication, and as required also for the mathematical further processing, of the measured difference in time.

In the apparatus according to the invention, for a known speed of the ultrasound, there may be immediately determined from the measured time differential, the difference in the distances (as viewed in the transmitter-receiver directions) of the first and second transmitter-receivers from the flowing medium, ($\Delta s = c \Delta t/2$, wherein $\Delta s$ is the difference between the distances, $c$ the speed of the ultrasonics, and $\Delta t$ the measured time differential). From this determined difference between the distances, as well as the known mutual spacing between the two transmitter-receivers, in accordance with simple trigonometric concepts, there may again be directly calculated the entry angle of the ultrasonics into the medium (for example $tg\phi = a/\Delta s$, wherein $\phi$ represents the entry angle, and a the spacing between the two transmitters). The now known angle $\phi$ may then be immediately considered as a corresponding correction factor in the determination of a value which is proportionate to the flow velocity of the medium. The invention also facilitates that, by means of the Doppler effect, the velocity may be determined independently of the angle and, namely, with a transmitter-receiver system which, due to the closely adjacent extending parallel transmitter-receiver lobes, renders possible the positioning of a suitable blood vessel at a suitable application location, and at a suitable body depth wherein, in effect, all of previously described advantages observed from the 90°-position of the transmitting directions of the receiver according to German Published Specification No. 1,798,104 are no longer present. The apparatus according to the invention further facilitates the determination of a value which is proportional to the flow velocity of the medium from the Doppler-frequency spectrum from either one or the other transmitter-receiver. Consequently, from the received Doppler-frequency spectrum there need no longer be transmitted in total two separate median frequencies, as in the apparatus according to German Published Specification No. 1,798,104. Accordingly, the thus required practical construction is only one-half that of the apparatus of the German Specification.

The angle $\phi$ in the above-described calculating steps may be manually determined, for example, by means of a slide rule. In order to accelerate the calculating procedure it is, however, advantageous to employ an electric calculator, which calculates the correction factor for the proportional value considerate of the entry angle of the incoming ultrasound beam into the medium, directly from the measured time differential, the speed of the ultrasound, and the spacing between the two transmitters-receivers.

Since, in accordance with German Published Specification No. 1,798,104, the value which is proportional to the flow velocity of the medium is directly proportional to the cosine of the entry beam angle ($\cos \phi$), for simplicity's sake the proportional value should also be immediately corrected with the reciprocal thereof ($1/\cos \phi$). The calculator should, within the scope of the invention, be so constructed as to immediately calculate the correction factor from the time differential $\Delta t$, the flow velocity $c$ of the ultrasonic and the spacing $a$ between the two transmitter-receivers, into $$K = 1/\cos \phi = \sqrt{1 + tg^2} = 1 + \sqrt{(\frac{2a}{c\Delta t})^2},$$

and wherein a multiplier element should be included for multiplying the obtained proportional value with this calculated correction factor.

The time differential $\Delta t$ which is required for the calculation of the corrector factor may be measured by obtaining the difference between the elapsed time periods for the ultrasonics from the transmitting time point until the entry of the ultrasound reflected by the medium through timing elements separately for each transmitter-receiver. However, in accordance with a preferred embodiment of the invention, it may also be measured by a determination of the timewise interval between a particular first signal generated by the receipt of ultrasound reflected by the medium at one transmitter-receiver and a particular second signal generated by the receipt of ultrasound reflected by the medium at the other transmitter-receiver. It is thereby purposeful that the electrical impulses be generated in timewise dependence upon the time points, in which the ultrasound received from the medium always exceeds a preset intensity level which is of the same height for both transmitter-receivers. Here again, it is of advantage that, for each ultrasonic transmitter-receiver, the generating time point of the associated electrical impulse be determined by the time point at which the intensity of the particular Doppler signal, which is won through usual demodulation of the received ultrasound, exceeds a threshold value which is set at a level in a threshold value discriminator so as to be at the same level for both transmitter-receivers. The threshold of this threshold value discriminator thereby is dynamically regulatable in dependence upon the intensity fluctuations of the received ultrasound or, respectively, Doppler signals on a preset constant percentage value of the particular instantaneously present intensity peak value, or a median value of the intensity measured over a known time period, preferably at 50% of the peak value of the intensity. For controlling the received ultrasound intensity at the threshold value, in a preferred embodiment of the invention, each threshold value discriminator associated with each of the transmitter-receivers including an electronic gate, which is controllable for a short period in its opened condition by means of a control arrangement during the time interval of receipt of the ultrasound, and whole opening time point during the time period of ultrasound receipt is so long displaceable through the control arrangement in dependence upon the deviation from the particular attained instantaneous value with respect to the intended percentage value, until the opening time point of the gate coincides with the actual time point of the intended percentual value. The control arrangement, for that purpose, includes an impulse generator which delivers short-term opening impulses to the two electronic gates in beat with the ultrasound transmission, as well as an impulse delay installation for the opening impulses which is connected between the gates and the impulse generator, whose impulse delay times are so lengthwise displaceable in dependence upon the instantaneous value-percentage value-deviations of the received ultrasound intensity, until the occurrence time point for the appearing delayed opening impulses at the gates coincide with the particular occurrence time point for the intended percentual value of the intensity at both transmitter-receivers. The so delayed opening impulses for the first and second electronic gate thereby form first and second impulses at the first and second transmitter-receivers the exceeding of the threshold intensity values which are of equal levels for the received ultrasound for both transmitter-receivers.

BRIEF DESCRIPTION OF THE DRAWINGS

Reference may now be had to a preferred embodiment of the present invention, taken in conjunction with the accompanying drawings; in which.

DETAILED DESCRIPTION

Figure 1:
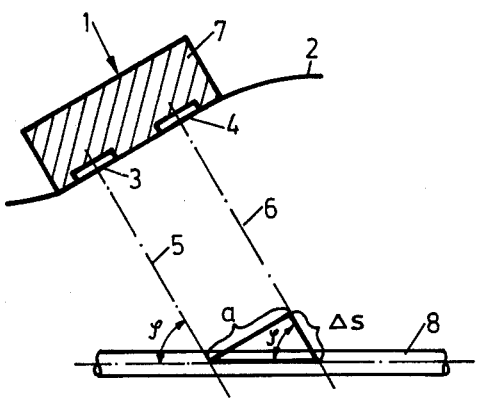
FIG. 1 illustrates an ultrasonic receiver according to the present invention.

In FIG. 1 of the drawings, an ultrasound sensor 1 is positioned on the skin 2 of a patient's body. The sensor consists of two ultrasonic vibrators 3 and 4 (piezoelectric crystal plates), which are positioned adjacent each other at a predetermined spacing, with their transmitting-receiving directions 5, respectively, 6 being located in parallel to each other on the applicating side of a support 7 which is, for example, formed of plastic material.

Both of the vibrators 3 and 4 serve for the beaming or transmission of ultrasound impulses into a blood vessel 8 which is located in the tissues beneath the body skin 2, as well as for receiving the reflected impulses from the blood flowing through the blood vessel 8 (echoimpulses).

Due to the illustrated inclined positioning of the vibrators 3 and 4 relative to the blood vessel 8, a difference in distance is formed between the two vibrators and similar points in the blood vessel, which is designated by $\Delta s$. This difference in distance, $\Delta s$, directly depends upon the magnitude of the angles of inclination $\phi$ of the vibrators 3, 4 with respect to the blood vessel 8 (entry angle $\phi$ for the ultrasound impulses into the blood vessel), and is tied to the latter through the trigonometric relationship $\tan\phi = a/\Delta s$. If $\Delta s$ is known, then in a simple manner, pursuant to $$1/\cos\phi = \sqrt{1 + tg^2} = 1 + \sqrt{\left(\frac{a}{\Delta s}\right)^2}$$

there may be determined the angle-independent measurement of the blood flow velocity necessary correction factor for Doppler frequency providing measure of the blood flow velocity (frequency drift between transmitted and received ultrasound)

$$\Delta f = \frac{2vf_0}{c}\cos\phi$$

($v$ = blood flow velocity, $f_0$ = frequency of the emitted ultrasound impulses, $c$ = the speed of the ultrasound impulses).

The distance difference $\Delta s$ is ascertained, for a known speed $c$ of the ultrasound impulses, from the impulse cycle time differential $\Delta t$ in accordance with $$\Delta s = \frac{c}{2}\Delta t.$$

For a known cycle time differential $\Delta t$ there is thus obtained the correction factor for $$K = 1/\cos\phi = 1 + \sqrt{\left(\frac{2a}{c\Delta t}\right)^2}.$$

Figure 2:
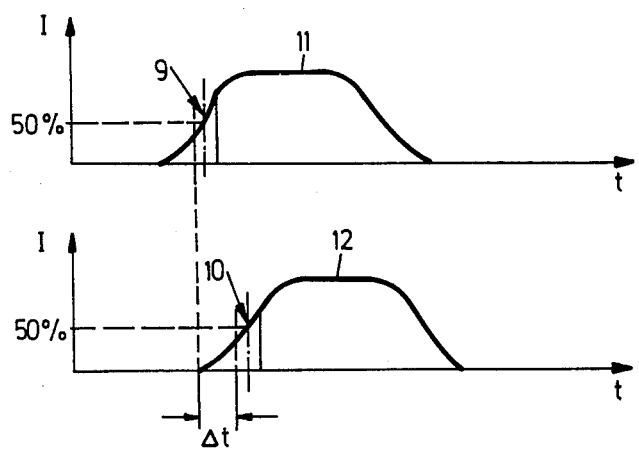
FIG. 2 is a graphical representation of the ultrasound impulses with respect to time.

In order to obtain the time differential $\Delta t$ for a pulsating transmitting operation of the vibrators 3 and 4, there is observed the intensity I (output) of the Doppler-displaced echo impulses which are reflected by the blood. In any case, it will pulsate, as indicated in FIG. 2, at less steeper pulse cycles or increases, since the transmitting impulse end portion require a finite time, until they have traversed the entire blood vessel. Therefore, if during the searching period there is regulated a periodic interval, (for example, as illustrated in FIG. 2 by 9 and 10) in both receiver channels at equal points in the rising slopes of the particular Doppler-displaced echo signals, designated in FIG. 2 by 11 and 12, for example at the 50% value at which the slope rise is the steepest then the difference $\Delta t$ between the scanning time points for the period intervals precisely corresponds to the ascertained cyclical time differential.

Figure 3:
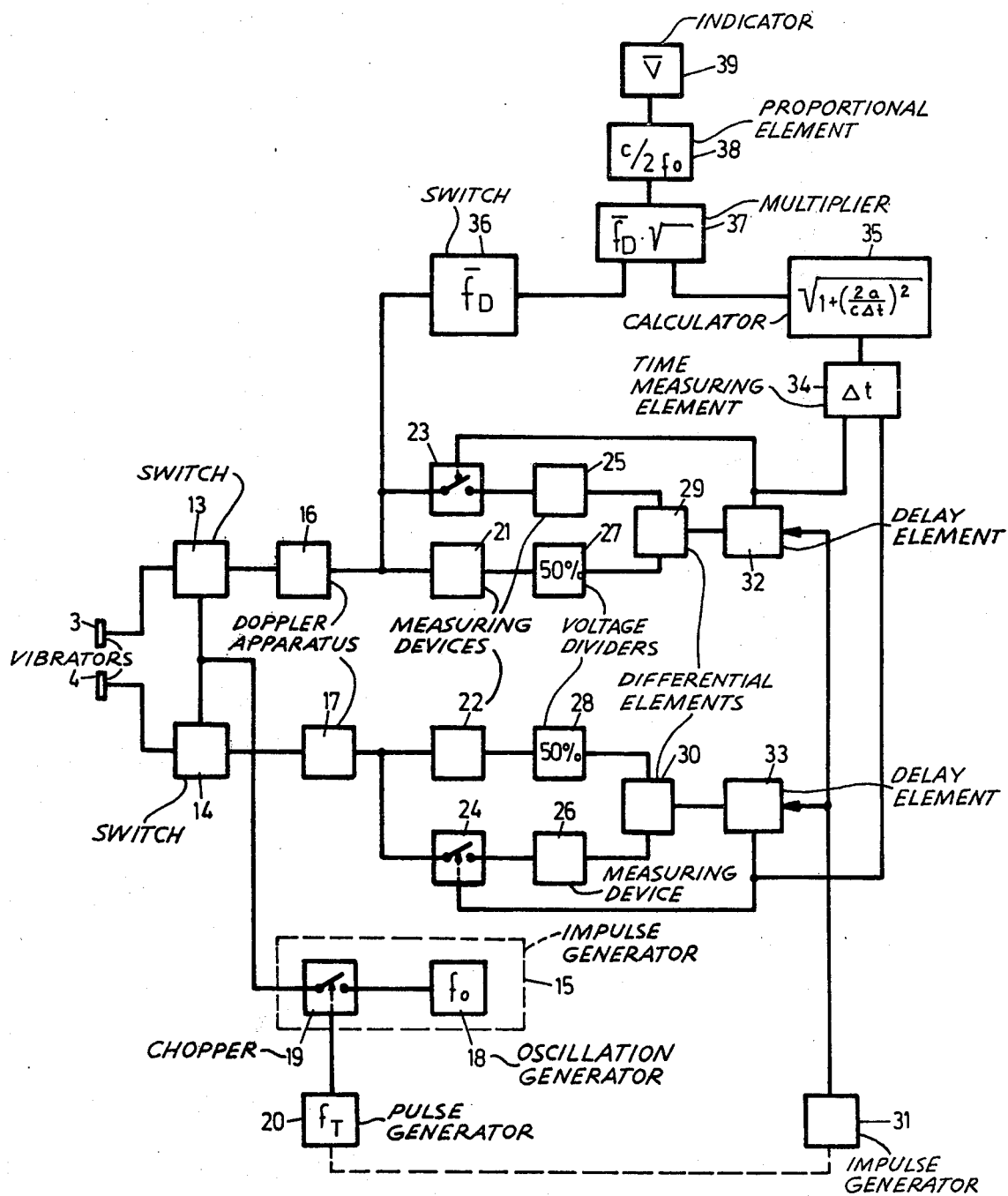
FIG. 3 is a schematic diagram of an installation according to the invention.

The generation and regulation of the period intervals is more closely explained in FIG. 3, which shows, in principle, an exemplary embodiment of the entire inventive apparatus in a schematic circuit diagram.

In FIG. 3 both transmitter-receiver vibrators 3 and 4 are each respectively connected on the one hand, through respective signal switches 13 and 14 (bridging circuit) with a high-frequency impulse generator 15 for supplying the vibrators 3 and 4 in the transmitting operation, as well as, on the other hand, with Doppler apparatus 16 and, respectively, 17 for obtaining the Doppler signals from the frequency slip between the transmitted and received ultrasound impulses. The high-frequency impulse generator 15 consists of a high-frequency oscillation generator 18 (frequency of the high frequency oscillations is, for example, $f_0$ = 5 MHz) as well as a prior connected-in chopper 19 (for example, an AND-element), which chops the high frequency oscillations of the high-frequency generator 18 into corresponding high-frequency impulses in the beat $f_T$ of a pulse generator 20, for example, in a 30 kHz-beat having a pulse-interval-relationship of 1:1. The Doppler apparatus 16, 17 are constructed in the usual manner, in effect meaning, that they contain the high-frequency amplifiers for the generated electrical echo signals produced by the vibrators 3 and 4 during the receiving operation; a demodulator consisting of a rectifier arrangement with after-connected low-pass filter (for example an LC-low-pass filter), as well as a low frequency amplifier, for the Doppler signals which are obtained through the demodulation.

Each of the respective Doppler apparatus 16 and 17 is directly connected with first intensity measuring devices 21, 22, as well as through switch 23 and 24, respectively, to second intensity measuring devices 25 and 26. The intensity measuring devices 21 and 22, respectively, in turn, have connected thereto element 27 and 28 (voltage dividers) for determining the particular 50%-value of the intensity level at the intensity measuring devices 21 and 22, while connected to the outputs between these elements and the second energy measuring devices 25 and 26 there are respectively located differential generators 29 and 30 (operating amplifiers) which forms the particular difference between the energy values at the energy measuring devices 25 and 26, and the ascertained 50%-values at the elements 27 and 28.

The switches 23 and 24 serve to produce the above-mentioned intervals so as to achieve the time point occurrences for the particular 50%-values. In order to regulate the closure times for the switches 23 and 24 at the produced time points for the 50%-values, there are employed short-term impulses which are generated by an impulse generator 31 in the beat of the ultrasonic impulse transmission frequency, in effect, synchronous with the beat $f_T$ (for example, 30 kHz) of the timing or beat generator 20, and which are transmitted by means of respective delay elements 32 and 33 (for example, an integrator with a switched-in voltage-controlled monostable oscillating member) at greater or lesser delays to the switches 23 and 24 for effecting the short-term closures thereof. The delay periods for the delay elements 32 and 33 thereby are variable in dependence upon the output levels of the differential elements 29 and 30.

The switches 23 and 24, with the thereto connected intensity measuring devices 25 and 26 may, instead of being connected to the outputs of the Doppler apparatus 16 and 17, (low-frequency components), be connected, for example, to the outputs of the high-frequency amplifiers of these apparatus. In that instance, a further demodulator must follow each of the particular switches 23 and 24. Independently of the particular switching relationship, the individual switching elements between the vibrators 3 and 4 must be so wide band designed when leading to the switches 23, 24 (for example, 1 MHz) so that the impulses received in the beat of the timing frequency $f_T$, for example, in 30 kHz beat, are transmitted to the switches 23 and 24 without excessive linear distortions. Behind the switches 23 and 24 there must further be provided filter means (not shown) which eliminate the switching frequency $f_T$ (for example, 30 kHz), as well as the therewith related harmonic vibrations. The Doppler signals which are received by, respectively, the intensity measuring devices 21, 22, as well as 25 and 26, are additionally output-wise weakened due to pulsating operation in contrast with the durational sequence-produced Doppler signals for the particular pulse ratio of the pulse sequences. In order to obtain comparable intensity values in the particular measuring channels, the respective Doppler signal in the particular channel must again be amplified for the reciprocal pulse ratio.

A time measuring element 34 is connected into the impulse inlet conduits between the delay elements 32 and 33, as well as between the respective switches 23 and 24 which measures the particular time intervals between the different delayed impulses of the impulse generator 31 received at the outputs of the delay element 32 and delay element 33. This time measuring element 34, in turn, has connected thereto a calculating installation 35 including a multiplying, dividing, squaring, summating, as well as erasing element, for calculating the correction factor $$K = \sqrt{1 + (\frac{2a}{c\Delta t})^2}$$

from the time differential $\Delta t$ obtained through the time measuring element 34, the known spacing a between the two vibrators 3 and 4, as well as the known running or delay time c of the ultrasound impulses.

The output of the Doppler apparatus 16, additionally thereto, is connected with a switching arrangement 36 which serves for the determination of the relevant median frequency $f_D$ for the median blood flow velocity in the blood vessel 8 from the frequency spectrum of the Doppler signals which are received from the apparatus 16. The switching arrangement 36 preferably corresponds to the previously mentioned switching arrangement disclosed in German Laid-Open Specification No. 1,791,191. A multiplier element 37 facilitates the multiplication of the output values of the switching arrangement 36 to $$\overline{f}_D = \sqrt{1 + (\frac{2a}{c\Delta t})^2},$$

wherein a proportional element 38, for example, a potentiometer forms the product $$c/2f_o \times \overline{f}_D \times \sqrt{1 + \frac{2a}{c\Delta t}^2},$$

which product is directly equivalent to the to be determined median blood flow velocity $\overline{v}$, and including an indicator apparatus 39 for the thus ascertained median blood flow velocity $\overline{v}$.

The operation of the apparatus shown in the schematic switching diagram in FIG. 3 is as follows:

Both ultrasonic vibrators 3 and 4 respectively beam or transmit concurrent ultrasound impulses into the blood vessel 8 in the beat $f_T$ of the timing or pulse generator 20. The ultrasound impulses (echo impulses) deflected by the flowing blood are transmitted to the Doppler apparatus 16 and 17 for obtaining of the Doppler signals. For each received Doppler signal, the intensity is determined in the intensity measuring devices 21 and 22, and subsequently the 50%-values are formed in the elements 27 and 28. This 50%-value is continually compared with the instantaneous values of the Doppler signal intensities received at the outputs of the intensity measuring device 25 and 26 for short-terms for each closing of the switches 23 and 24 (for example, 30 kH-beat). Depending upon the magnitude of the thus obtained instantaneous value-percentage value-deviation, the delay periods for the delay elements 32 and 33 forming the impulses of the impulse generator 31, are separately longitudinally varied for each delay element to such an extent until the closing time points for the switches 23, 24, coincide with the respective exit time point for the 50%-energy value of the Doppler signals in the particular receiving channels. The settable spacing between the impulses of the delay elements 32 and the delay element 33 at the time point of this coincidence is the sought after cyclical time differential $\Delta t$ for the calculation of the angle correction factor.

The above-described exemplary embodiment, in particular, serves for blood flow measurement. However, it is naturally also applicable, in the same manner, to the measurement of organ movement (for example, heart beat), and for practical or commercial purposes (measurement of velocity of media, for example, in flexible hoses).

While there has been shown what is considered to be the preferred embodiment of the invention, it will be obvious that modifications may be made which come within the scope of the disclosure of the specification.

What is claimed is:

1. In an apparatus for measuring the velocity of media flowing in conduits, such as blood in its vessels, through the intermediary of ultrasound pursuant to the Doppler effect-method, at least two ultrasonic transmitter-receivers for projecting inclined beams of ultrasound into said medium and receiving ultrasound reflected by said medium; said transmitter-receivers being positioned proximate each other at a predetermined spaced relationship and oriented so that their respective transmitting and receiving directions extend in parallel to each other, and means for determining a value proportionate to the flow velocity of said medium from the frequencies of the emitted and received ultrasound the improvement comprising; time measuring means connected to said transmitter-receivers for detecting the time interval between timewise successively received sound waves and particularly for measuring the time differential between receipt of the ultrasound reflected by said medium at, respectively, a first and a second of said transmitter-receivers upon concurrent beaming of ultrasound from both said transmitter-receivers into said medium; and means for mathematical processing of said measured time differential.

2. An apparatus as claimed in claim 1, said mathematical processing means comprising a calculating arrangement for calculating a correction factor for the proportionate value, considerate of the entry angle of the ultrasound transmitted into said medium, from said measured time differential, the speed of the ultrasound, and the spacing between said first and second transmitter-receivers.

3. An apparatus as claimed in claim 2, said calculating arrangement calculating said correction factor in accordance with the equation $$K = \sqrt{1 + \left(\frac{2a}{c\Delta t}\right)^2}$$

wherein K is the correction factor, a is the distance between said first and second transmitter-receivers, c is the speed of the ultrasound, and $\Delta t$ is the measured time differential; and including a multiplier element for multiplying said proportional value with the calculated correction factor.

4. An apparatus as claimed in claim 1, said time measuring means determining said time differential in response to the difference between the delay times for said ultrasound obtained separately for each said transmitter-receiver from the emitting time point until receipt of the ultrasound reflected from said medium.

5. An apparatus as claimed in claim 1, said time measuring means determining the measured time differential between a particular first impulse generated in response to ultrasound reflected by said medium received by a first of said transmitter-receivers, and a particular second impulse generated in response to ultrasound reflected by said medium received by a second of said transmitter-receivers.

6. Apparatus as claimed in claim 5, each said impulse being generated in timewise dependence upon the time points at which the ultrasound reflected from said medium exceeds an intensity level of equal value for both of said transmitter-receivers.

7. Apparatus as claimed in claim 6, comprising threshold value discriminating means for determining the generating time point for said first and second impulses associated with each said ultrasonic transmitter-receiver at the time point in which the intensity of a particular Doppler signal obtained by demodulation of the received ultrasound exceeds a threshold value which is equal for both transmitter-receivers.

8. Apparatus as claimed in claim 7, said threshold value of each threshold discriminating means for each respective transmitter-receiver being dynamically adjustable in dependence upon intensity fluctuations of the received ultrasound and Doppler signals to a preset constant percentage of the particular instantaneous intensity peak value.

9. Apparatus as claimed in claim 8, each said threshold value discriminating means including an electronic gate, control means for maintaining said gates in short-term opened condition during the interval of receiving the ultrasound for obtaining the instantaneous value of the received intensity, the opening time point for said gates during the time interval of receiving ultrasound being displaceable by said control means in dependence upon a deviation of the particular instantaneous value from the desired percentage for an extent until the opening time points for said gates coincide with the incidental time point for the desired percentage.

10. An apparatus as claimed in claim 9, said control means including an impulse generator transmitting open impulses of short duration to said electronic gates in beat with said ultrasound transmission; and impulse delay means for said opening impulses connected intermediate said gates and said impulse generator, the impulse delay times being variable in dependence upon the instantaneous value-percentage-deviations of the receiver ultrasound in a longitudinal direction to an extent until delayed opening impulses coincide with the particular incidental time point for the desired percentage of the intensity of the ultrasound received at both of said transmitter-receivers.

11. An apparatus as claimed in claim 10, the delayed opening impulses for said first and second electronic gates forming first and second impulses at both transmitter-receivers for exceeding the equally high generated threshold intensity value of the received ultrasound at said first and second transmitter-receiver.

12. Apparatus as claimed in claim 7, said threshold value of each threshold discriminating means for each respective transmitter-receiver being dynamically adjustable in dependence upon intensity fluctuations of the received ultrasound and Doppler signals for a measured median value of the intensity over a known time period.

13. Apparatus as claimed in claim 12, said median value being 50% of the peak value of the intensity.

* * * * *